United States Patent [19]

Lidgate et al.

[11] Patent Number: 5,688,529

[45] Date of Patent: Nov. 18, 1997

[54] MYCOPHENOLATE MOFETIL HIGH DOSE ORAL SUSPENSIONS

[75] Inventors: Deborah Marilyn Lidgate, Los Altos; Li-hua Wang-Kessler, Palo Alto; Bindu Joshi, Milpitas; Sayee Gojanan Hegde, Los Angeles; Leo Gu, Saratoga, all of Calif.

[73] Assignee: Syntex (U.S.A) Inc., Palo Alto, Calif.

[21] Appl. No.: 412,645

[22] Filed: Mar. 29, 1995

Related U.S. Application Data

[63] Continuation-in-part of Ser. No. 130,343, Oct. 1, 1993, abandoned.

[51] Int. Cl.$^6$ .............................. A61K 9/14; A61K 9/16
[52] U.S. Cl. ..................... 424/489; 424/439; 514/777; 514/781; 514/937; 514/782
[58] Field of Search ........................ 424/489, 439; 514/777, 781, 937, 782

[56] References Cited

U.S. PATENT DOCUMENTS

| | | | |
|---|---|---|---|
| 3,880,995 | 4/1975 | Jones | 424/180 |
| 4,753,935 | 6/1988 | Nelson et al. | 514/233.5 |

FOREIGN PATENT DOCUMENTS

| | | |
|---|---|---|
| 21 58 824 | 6/1972 | Germany. |
| 1 157 100 | 7/1969 | United Kingdom. |
| 92/02229 | 2/1992 | WIPO. |

*Primary Examiner*—Thurman K. Page
*Assistant Examiner*—James M. Spear
*Attorney, Agent, or Firm*—Heller Ehrman White & McAuliffe

[57] ABSTRACT

High dose, dry granulations or powder blends and aqueous oral suspensions of mycophenolate mofetil or mycophenolic acid, contain: active compound (7.5-30%), suspending/viscosity agent, sweetener, flavor, buffer (to a pH of 5-7.5), and optionally contain flavor enhancer, wetting agent, antimicrobial agent and color.

18 Claims, No Drawings

MYCOPHENOLATE MOFETIL HIGH DOSE ORAL SUSPENSIONS

CROSS-REFERENCE TO RELATED APPLICATION

This application is a continuation-in-part of our application Ser. No. 08/130,343, filed Oct. 1, 1993, now abandoned.

FIELD OF THE INVENTION

The present invention relates to mycophenolate mofetil and mycophenolic acid, particularly to improved formulations thereof, and specifically to high dose oral suspension formulations. The invention is also directed to methods of manufacturing the formulations.

BACKGROUND INFORMATION

Mycophenolic acid ("MPA") was initially described as a weakly-active antibiotic found in the fermentation broth of *Penicillium brevicompactum*, having the following structure:

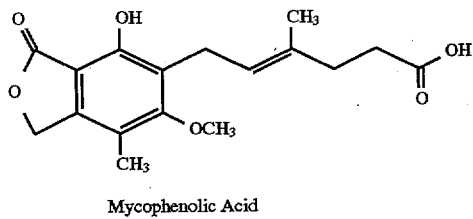

Mycophenolic Acid

MPA and certain related compounds, such as mycophenolate mofetil (the morpholinoethyl ester of MPA), having the following structure:

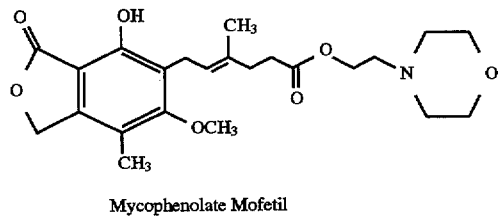

Mycophenolate Mofetil have more recently been described as having particularly advantageous therapeutic properties, e.g., as immunosuppressant drugs. See, for example, U.S. Pat. Nos. 3,880,995; 4,727,069; 4,753,935; and 4,786,637, all incorporated herein by reference.

MPA and mycophenolate mofetil, notwithstanding the improved oral bioavailability characteristics of the latter, require daily doses on the order of 2.0 to as much as 3.5 or 4.0 grams per day (or even 5.0 grams per day in the case of MPA, for example as described in U.S. Pat. No. 3,880,995) depending upon the patient and the disease state being treated. Using a conventional dosage formulation containing 250 mg in a standard size 1 (0.48 cc volume) capsule, a patient receiving a 3.0 gram daily dose is required to take twelve capsules each day, giving rise to patient convenience and compliance concerns.

Coarse dispersions, such as oral suspensions, contain a finely divided insoluble material suspended in a liquid medium. These are described, for example, in Remington's Pharmaceutical Sciences (Fifteenth Edition, Chapters 22 and 83, 1975) and for specific products in the Physicians' Desk Reference (46th Edition, Medical Economics Date, 1992). Oral suspensions are known for ease of administration, for example, to children or elderly adults, and are not typically employed for the purpose of attaining high dose formulations. Certain "ready to use" suspension vehicles, such as Ora-Plus™ combined with Ora-Sweet™ (both available from Paddock Laboratories, Inc. of Minneapolis, Minn.) are available for extemporaneous compounding needs, but their suitability for any particular active agent must be determined on a case by case basis. Moreover, such vehicles are contraindicated for long term stability and, therefore, intended only for short term use.

Oral suspensions of mycophenolate mofetil have been described, for example, in U.S. Pat. No. 4,753,935 (see, Example 7), but at a relatively low dose incorporating 1 gram of active compound in 100 mL. While such suspensions are functional, they are subject to the same patient convenience and compliance concerns as prior low dose capsule formulations.

It has remained desired to provide high dose oral formulations for MPA and mycophenolate mofetil, particularly in view of the relatively high daily doses required for administration.

SUMMARY OF THE INVENTION

The present invention concerns high dose oral suspensions of mycophenolate mofetil, high dose oral suspensions of mycophenolic acid, and methods of manufacture therefor.

In one aspect, the invention relates to high dose oral suspensions having a composition as follows:

| Ingredient | % wt/vol |
|---|---|
| mycophenolate mofetil or mycophenolic acid | 7.5–30.0 |
| suspending/viscosity agent | 0.1–3.0 |
| wetting agent | 0–0.5 |
| sweeteners | 30.0–70.0 |
| flavor | 0.1–2.0 |
| flavor enhancer/bitter maskant | 0–1.0 |
| buffer to pH 5.0–7.5 | 0.15–2.0 |
| antimicrobial agent | 0–10.0 |
| color | 0–0.03 |
| purified water | q.s. to 100 |

In a presently preferred aspect, the invention relates to a high dose oral suspension of mycophenolate mofetil having a composition as follows:

| Ingredient | % wt/vol |
|---|---|
| mycophenolate mofetil | 20 |
| hydroxypropylmethylcellulose | 0.25 |
| microcrystalline cellulose | 0.25 |
| xanthan gum | 0.1 |
| sorbitol, 70% solution | 30–50 |
| Lycasin* (maltitol syrup) | 10–30 |
| sucrose | 0–10 |
| fructose | 0–10 |
| aspartame | 0–0.5 |
| lecithin | 0–0.1 |
| citric acid | 0.02–0.25 |
| sodium phosphate dibasic | 0.19–0.67 |
| methyl paraben | 0–0.18 |
| propyl paraben | 0–0.02 |
| flavor [selected from grape, (opt. w/anise), cherry, strawberry, or mint] | 0.3–1.0 |
| Magnasweet* | 0–1 |
| color(s) (selected from red 28, red 40, blue 1, blue 2, or green 3) | 0.005 |
| purified water | q.s. to 100 |

In another presently preferred aspect, the invention relates to a high dose oral suspension of mycophenolate mofetil having a composition as follows:

| Ingredient | % wt/vol |
| --- | --- |
| mycophenolate mofetil | 20 |
| microcrystalline cellulose | 0.2 |
| xanthan gum | 0.1 |
| sorbitol, 70% solution | 30–50 |
| Lycasin* (maltitol syrup) | 10–30 |
| sucrose | 0–10 |
| fructose | 0–10 |
| aspartame | 0–0.5 |
| lecithin | 0–0.5 |
| citric acid | 0.02–0.25 |
| sodium phosphate dibasic | 0.15–1.0 |
| methyl paraben | 0–0.2 |
| propyl paraben | 0–0.02 |
| flavor (selected from grape (opt. w/anise), cherry, strawberry, mint, orange, berry, or mixed fruit) | 0.1–3.0 |
| Magnasweet* | 0–1 |
| color(s) (selected from red 28, red 40, red #3, yellow #6, blue 1, blue 2, or green 3) | 0.02 |
| purified water | q.s. to 100 |

In another aspect, the invention relates to a dry granulation or powder blend formulation of mycophenolate mofetil for constitution with water to give a high dose oral suspension, having a composition as follows:

| Ingredient | mg/mL* |
| --- | --- |
| mycophenolate mofetil or mycophenolic acid | 75–300 |
| suspending/viscosity agent | 1–30 |
| wetting agent | 0–10 |
| sweeteners | 1–1200 |
| flavor | 0.1–100 |
| flavor enhancer/bitter maskant | 0–50 |
| buffering agents | 0–25 |
| antimicrobial agent | 0–10 |
| color | 0–2 |

(*concentration after constitution with water).

In a presently preferable aspect, the invention relates to a dry granulation formulation of mycophenolate mofetil for constitution with water to give a high dose oral suspension, having a composition as follows:

| Ingredient | mg/mL* |
| --- | --- |
| mycophenolate mofetil | 200 |
| xanthan gum | 0.5–1.5 |
| collodial silicon dioxide | 5–10 |
| sorbitol | 0–550 |
| aspartame | 0–3 |
| soy lecithin | 1–2 |
| citric acid | 0–1.5 |
| sodium citrate | 0–20 |
| sodium methyl paraben | 0–10 |
| flavor ((selected from grape (opt. w/anise), cherry, strawberry, mint, orange, berry, or mixed fruit) | 0.1–3.0 |
| color (red, blue, and/or yellow to complement the flavor) | 0–0.2 |

(*concentration after constitution with water).

DETAILED DESCRIPTION OF THE INVENTION

Definitions and General Parameters

The following definitions are set forth to illustrate and define the meaning and scope of the various terms used to describe the invention herein.

Reference to the active agent employed in the formulations of the present invention, "mycophenolate mofetil," is intended to include the pharmaceutically acceptable salts thereof.

The term "effective amount" means a dosage sufficient to provide treatment for the disease state being treated. This will vary depending on the patient, the disease and the treatment being effected.

The term "% wt/vol" or "percent weight/volume" refers to the amount of excipient and/or drug substance, measured by weight (grams), that is contained in the final volume (milliliters) of a suspension. The amount of excipient and/or drug substance is expressed as a percent of the total, final volume of the liquid product, or the constituted liquid product.

The term "dry granulation" refers to the formation of an agglomerate, and is defined herein to include powder blends in which the components are mixed together.

Manufacturing Parameters

The term "q.s." means adding a quantity sufficient to achieve a stated function, e.g., to bring a solution to the desired volume (i.e., 100%).

Unless specified to the contrary, the procedures described herein take place at atmospheric pressure within a temperature range from 5° C. to 100° C. (preferably from 10° C. to 50° C.; most preferably at "room" or "ambient" temperature, e.g., 20° C.).

Unless otherwise specified, the composition percentages, times and conditions are intended to be approximate, e.g., add about 10% wt/vol at about atmospheric pressure within a temperature range of about 5° C. to about 100° C. (preferably from about 10° C. to about 50° C.; most preferably about 20° C.) over a period of about 1 to about 10 hours (preferably about 5 hours). Parameters given in the Examples are intended to be specific, not approximate.

Materials

Mycophenolate mofetil can be made as described in U.S. Pat. No. 4,753,935, previously incorporated by reference. It is presently preferred to make mycophenolate mofetil as described in U.S. Pat. No. 5,247,083, incorporated herein by reference. Mycophenolic acid is commercially available, e.g., from Sigma Chemical Company, St. Louis, Mo. The sources of various excipients are disclosed below, e.g., where the material is not commonly available or when the product of a particular source is preferred.

Suspending and/or viscosity increasing agents useful in the formulations of the invention include, for example: hydroxypropyl methylcellulose (preferably USP: hydroxypropyl methylcellulose 2910); xanthan gum (preferably NF: xanthan gum, and most preferably Keltrol® CR, available from Kelco, San Diego, Calif.); microcrystalline cellulose (which is a colloidal suspending agent, preferably NF: microcrystalline cellulose, and most preferably Avicel® RC-591, available from FMC Corporation, Philadelphia, Pa.); sodium carboxymethylcellulose (preferably USP: carboxymethylcellulose sodium, or BP: camellose sodium or sodium carboxymethylcellulose); and colloidal silicon dioxide (preferable NF: colloidal silicon dioxide, and more preferably Cab-O-Sil® M-5, available from Cabot Corporation, Tuscola, Ill.).

Wetting agents useful in the formulations of the invention include, for example: lecithin (compendial or non-compendial soy lecithin) and poloxamer (available as pluronic F68 from BASF Wyandotte Corporation, Parsippany, N.J.).

Sweeteners useful in the formulations of the invention include, for example: sorbitol, 70% solution (preferably USP: sorbitol solution); maltitol syrup (preferably USP or NF, most preferably Lycasin®, available from Roquette Corporation, Gurnee, Ill.); sucrose (preferably NF or BP/EP); fructose (preferably USP); aspartame (preferably NF); xylitol (preferably compendial grade); mannitol (preferably USP or BP); sorbitol, powder (preferably NF or BP); maltitol, crystalline (non-compendial, or preferably Maltisorb® SF, available from Roquette Corporation, Gurnee, Ill.). In cases where there is a choice of physical form, the liquid sweeteners are preferably used for the suspension formulations, and the dry sweeteners are preferably used for the dry granulation. The sweeteners (except aspartame) can also function as viscosity-increasing agents and/or as antimicrobial preservatives).

Flavors useful in the formulations of the invention include, for example: mint, strawberry, cherry, orange, berry, mixed fruit, and grape (optionally mixed with anise). They are available from Tastemaker, Cincinnatti, Ohio; Crompton & Knowles Corporation, Mahwah, N.J.; and International Flavors & Fragrances Inc., Camden, N.J.

Flavor enhancers (or bitter maskants) useful in the formulation of the invention include, for example Magnasweet® (available from MacAndrews & Forbes Company, Camden, N.J.).

Buffers useful in the formulations of the invention include as components, for example, citric acid (preferably USP) and sodium phosphate dibasic (preferably USP), and sodium citrate (preferably USP).

Antimicrobial agents useful in the formulations of the invention include, for example: sodium benzoate; sodium methyl paraben (preferably NF: sodium methyl paraben); methyl paraben (preferably NF: methyl paraben, or BP: methyl hydroxybenzoate, or EP: methylis parahydroxybenzoas); propylparaben (preferably NF: propylparaben, or BP/EP: propyl hydroxybenzoate); and potassium sorbate (preferably NF or BP).

Dyes (or colors) useful in the formulations of the invention include, for example: FD&C red 28, FD&C red 40, FD&C red 3, FD&C blue 1, FD&C blue 2, FD&C yellow 6, and FD&C green 3.

HIGH DOSE ORAL SUSPENSION

Composition

The high dose oral suspensions of the present invention have the following general composition:

| Ingredient | % wt/vol |
| --- | --- |
| mycophenolate mofetil or mycophenolic acid | 7.5–30.0 |
| suspending/viscosity agent | 0.1–3.0 |
| wetting agent | 0–0.5 |
| sweeteners | 30.0–70.0 |
| flavor | 0.1–2.0 |
| flavor enhancer/bitter maskant | 0–1.0 |
| buffer to pH 5.0–7.5 | 0.15–2.0 |
| antimicrobial agent | 0–10.0 |
| color | 0–0.03 |
| purified water | q.s. to 100 |

Particularly when the active agent is MPA, pH must be kept below 7.0 to avoid dissolution.

Presently preferred oral suspensions of the invention have the following composition:

| Ingredient | % wt/vol |
| --- | --- |
| mycophenolate mofetil | 20 |
| hydroxypropylmethylcellulose | 0.25 |
| microcrystalline cellulose | 0.25 |
| xanthan gum | 0.1 |
| sorbitol, 70% solution | 30–50 |
| Lycasin* (maltitol syrup) | 10–30 |
| sucrose | 0–10 |
| fructose | 0–10 |
| aspartame | 0–0.5 |
| lecithin | 0–0.1 |
| citric acid | 0.02–0.25 |
| sodium phosphate dibasic | 0.19–0.67 |
| methyl paraben | 0–0.18 |
| propyl paraben | 0–0.02 |
| flavor | 0.3–1.0 |
| Magnasweet* | 0–1 |
| color | 0.005 |
| purified water | q.s. to 100 |

Presently more preferred oral suspensions of the invention have the following composition:

| Ingredient | % wt/vol |
| --- | --- |
| mycophenolate mofetil | 20 |
| microcrystalline cellulose | 0.2 |
| xanthan gum | 0.1 |
| sorbitol, 70% solution | 30–50 |
| Lycasin* (maltitol syrup) | 10–30 |
| sucrose | 0–10 |
| fructose | 0–10 |
| aspartame | 0–0.5 |
| lecithin | 0–0.5 |
| citric acid | 0.02–0.25 |
| sodium phosphate dibasic | 0.15–1.0 |
| methyl paraben | 0–0.2 |
| propyl paraben | 0–0.02 |
| flavor | 0.1–1.0 |
| Magnasweet* | 0–1 |
| color | 0.02 |
| purified water | q.s. to 100 |

Manufacturing Method

1. To heated water (about 70° C.), the antimicrobial agent is added and dispersed, followed by the suspending and/or viscosity agents (preferably microcrystalline cellulose, followed by xanthan gum).
2. With mixing, the buffer(s) (preferably citric acid, followed by sodium phosphate dibasic) are dissolved, followed by sweetener(s), wetting agent(s), dye(s), flavor enhancer(s), and flavor(s).
3. The active compound (mycophenolate mofetil or MPA) is added to the mixture from step 2; the liquid was mixed well to form a suspension.

DRY GRANULATION FORMULATION

Composition

The dry granulation formulations of the present invention have the following general composition:

| Ingredient | mg/mL* |
| --- | --- |
| mycophenolate mofetil or mycophenolic acid | 75–300 |
| suspending/viscosity agent | 10–30 |

-continued

| Ingredient | mg/mL* |
|---|---|
| wetting agent | 3–10 |
| sweeteners | 200–1200 |
| flavor | 3–100 |
| flavor enhancer/bitter maskant | 0–50 |
| buffering agents | 0–25 |
| antimicrobial agent | 0–10 |
| color | 0–2 |

(*concentration after constitution with water)

A presently preferred dry granulation formulation has the following composition:

| Ingredient | mg/mL* |
|---|---|
| mycophenolate mofetil | 200 |
| sodium carboxymethylcellulose | 20 |
| sucrose | 0–700 |
| fructose | 0–700 |
| xylitol | 0–700 |
| mannitol | 0–1200 |
| sorbitol | 0–1080 |
| maltitol | 0–740 |
| pluronic F68 | 4–8 |
| flavor | 10 |
| potassium sorbate | 0–5 |
| color | 0–1 |

(*concentration after constitution with water)

A presently more preferred dry granulation formulation has the following composition:

| Ingredient | mg/mL* |
|---|---|
| mycophenolate mofetil | 200 |
| xanthan gum | 0.5–1.5 |
| colloidal silicon dioxide | 5–10 |
| sorbitol | 0–550 |
| aspartame | 0–3 |
| soy lecithin | 1–2 |
| citric acid | 0–1.5 |
| sodium citrate | 0–20 |
| flavor | 1–3 |
| sodium methyl paraben | 0–10 |
| color | 0–0.2 |

(*concentration after constitution with water)

Manufacturing Method

1. Mycophenolate mofetil, sweetener(s), wetting agent(s), and suspending and/or viscosity increasing agent(s) are weighed and combined in a mixer.
2. The dye(s) and buffer(s) are dissolved in water.
3. The solution of step (2) is added to the mixer bowl of step (1), until a desired granulation size is obtained.
4. The granulation is dried then milled to reduce particle size.
5. Using a blender, the suspending and/or viscosity increasing agent(s), flavor(s) and antimicrobial agent(s) are added.

When used as a pharmaceutical formulation to administer mycophenolate mofetil or mycophenolic acid, for example, the dry granulation formulation is added to water in an appropriate container. The container is then sealed, shaken to give a suspension, and administered orally.

Alternatively, the granulation is provided in a container, such that when constituted with an appropriate volume of water a supply of drug in suspension is provided for an extended period of time (e.g., 90 grams of mycophenolate mofetil provided in a bottle marked to be filled with purified water to a final volume of 450 mL, provides a 30 day supply). The supply of drug in suspension could also be provided in smaller sizes, e.g., 24 grams of mycophenolate mofetil provided in a bottle marked to be filled with purified water to a final volume of 120 mL (4 oz size), or 48 grams of mycophenolate mofetil provided in a bottle marked to be filled with purified water to a final volume of 240 mL (8 oz size).

Preferred Formulations

Presently preferred are the following formulations.

| Ingredient | % wt/vol |
|---|---|
| mycophenolate mofetil | 20 |
| hydroxypropyl methylcellulose | 0.25 |
| microcrystalline cellulose | 0.25 |
| xanthan gum | 0.1 |
| sorbitol solution | 50 |
| sucrose | 10 |
| Lycasin* | 10 |
| lecithin | 0.1 |
| methyl paraben | 0.036 |
| propylparaben | 0.004 |
| grape | 1.0 |
| anise | 0.01 |
| color (red 28: blue 1, 90:10) | 0.005 |
| citric acid | 0.0542 |
| sodium phosphate dibasic | 0.673 |
| purified water | q.s. to 100 | adjusted to a pH of 7, as a liquid suspension suitable for oral administration.

| Ingredient | % wt/vol |
|---|---|
| mycophenolate mofetil | 20 |
| microcrystalline cellulose | 0.2 |
| xanthan gum | 0.1 |
| sorbitol solution | 50 |
| sucrose | 10 |
| Lycasin* (maltitol syrup) | 10 |
| soy lecithin | 0.1 |
| methyl paraben | 0.1 |
| mixed fruit | 0.2 |
| color (to complement the flavor) | <0.002 |
| citric acid | 0.06 |
| sodium phosphate dibasic | 0.7 |
| purified water | q.s. to 100 | adjusted to a pH of 7, as a liquid suspension suitable for oral administration.

| Ingredient | mg |
|---|---|
| mycophenolate mofetil | 90,000 |
| sodium carboxymethylcellulose | 9,000 |
| sorbitol | 135,000 |
| sucrose | 45,000 |
| pluronic F68 | 1,800 |
| potassium sorbate | 2,250 |
| cherry | 4,500 |
| color (red 40:blue 1, 90:10) | 4.5 | in a container marked to be filled with purified water to a final predetermined volume of 450 mL.

| Ingredient | mg |
| --- | --- |
| mycophenolate mofetil | 90,000 |
| xanthan gum | 450 |
| colloidal silicon dioxide | 2,250 |
| soy lecithin | 450 |
| sorbitol | 247,500 |
| aspartame | 225 |
| sodium methyl paraben | 900 |
| berry flavor | 1,350 |
| color (FD&C red #3 | 13.5 |
| FD&C blue #1 | 2.7 | in a container marked to be filled with purified water to a final predetermined volume of 450 mL.

| Ingredient | mg |
| --- | --- |
| mycophenolate mofetil | 90,000 |
| xanthan gum | 450 |
| colloidal silicon dioxide | 2,250 |
| soy lecithin | 450 |
| sorbitol | 135,000 |
| aspartame | 450 |
| citric acid | 495 |
| sodium citrate | 4,500 |
| sodium methyl paraben | 900 |
| berry flavor | 1,350 |
| color (FD&C red #3 | 13.5 |
| FD&C blue #1 | 2.7 | in a container marked to be filled with purified water to a final predetermined volume of 450 mL.

| Ingredient | mg |
| --- | --- |
| mycophenolate mofetil | 90,000 |
| xanthan gum | 675 |
| colloidal silicon dioxide | 4,500 |
| soy lecithin | 900 |
| sorbitol | 180,000 |
| aspartame | 450 |
| sodium methyl paraben | 1,035 |
| mixed fruit flavor | 960 |
| color (FD&C red #3 | 3.6 |
| FD&C yellow #6) | 0.9 | in a container marked to be filled with purified water to a final predetermined volume of 450 mL.

| Ingredient | mg |
| --- | --- |
| mycophenolate mofetil | 90,000 |
| xanthan gum | 450 |
| colloidal silicon dioxide | 2,250 |
| soy lecithin | 450 |
| sorbitol | 247,500 |
| aspartame | 225 |
| citric acid | 495 |
| sodium citrate | 4,500 |
| sodium methyl paraben | 1,035 |
| mixed fruit flavor | 900 |
| color (FD&C red #3 | 3.96 |
| FD&C yellow #6) | 0.855 | in a container marked to be filled with purified water to a final predetermined volume of 450 mL.

| Ingredient | mg |
| --- | --- |
| mycophenolate mofetil | 90,000 |
| xanthan gum | 675 |
| colloidal silicon dioxide | 4,500 |
| soy lecithin | 900 |
| sorbitol | 180,000 |
| aspartame | 450 |
| citric acid | 495 |
| sodium citrate | 4,500 |
| sodium methyl paraben | 1,035 |
| orange flavor | 450 |
| color (FD&C yellow #6) | 90 | in a container marked to be filled with purified water to a final predetermined volume of 450 mL.

The above formulations can also be made up in smaller sizes (e.g., oz or 8 oz) by using appropriately smaller quantities. For example,

| Ingredient | mg |
| --- | --- |
| mycophenolate mofetil | 45,000 |
| xanthan gum | 225 |
| colloidal silicon dioxide | 1,125 |
| soy lecithin | 225 |
| sorbitol | 123,750 |
| aspartame | 112.5 |
| citric acid | 247.5 |
| sodium citrate | 2,250 |
| sodium methyl paraben | 517.5 |
| mixed fruit flavor | 450 |
| color (FD&C red #3 | 1.98 |
| FD&C yellow #6) | 0.43 | in a container marked to be filled with purified water to a final predetermined volume of 240 mL.

| Ingredient | mg |
| --- | --- |
| mycophenolate mofetil | 22,500 |
| xanthan gum | 112.5 |
| colloidal silicon dioxide | 562.5 |
| soy lecithin | 112.5 |
| sorbitol | 61,875 |
| aspartame | 56.25 |
| citric acid | 123.75 |
| sodium citrate | 1,125 |
| sodium methyl paraben | 258.75 |
| mixed fruit flavor | 225 |
| color (FD&C red #3 | 0.99 |
| FD&C yellow #6) | 0.22 | in a container marked to be filled with purified water to a final predetermined volume of 120 mL.

Testing, Administration and Utility

Testing

The following tests are performed to evaluate the suitability of formulation combinations made in accordance with the present invention. The testing procedures are known by those skilled in the art.
1. Time to constitute (for a dry granulation).
2. Ease of resuspendability of solid(s).
3. Appearance.
4. Amount of drug dissolved in continuous aqueous phase.
5. Chemical stability (percent label strength of drug substance).
6. Degradant(s) formed (e.g. mycophenolic acid from a suspension of mycophenolate mofetil).

7. Viscosity.
8. Density.
9. Freeze/thaw (aggregate formation).
10. Sedimentation rate.
11. Sedimentation volume.
12. Homogeneity of drug substance.
13. Particle size.
14. Antimicrobial efficacy (USP/BP test).
15. Gravitational and vibrational stresses (simulated shipping).
16. Chemical stability of antimicrobial preservative.

The following tests are performed to evaluate the acceptability of formulations made in accordance with the present invention. The testing procedures are known by those skilled in the art.

1. Ease of resuspendability of solid(s).
2. Appearance.
3. Chemical stability (percent label strength of drug substance).
4. % Degradant(s) formed over time.
5. Viscosity.
6. Density.
7. Homogeneity of drug substance.
8. Particle size.
9. Antimicrobial efficacy (USP/BP test).
10. Chemical stability of antimicrobial preservative.

Criteria for acceptability include those set forth below.

Ease of resuspendability—The suspension sediment should be loosely packed such that after minimal shaking the sediment redisperses and reforms the original suspension. From a practical standpoint, any sediment should redisperse within 10 seconds of minimal hand shaking.

Appearance—In a freshly prepared suspension, all solids should be evenly and homogeneously dispersed in the liquid phase. Over time, sedimentation will occur; and ideally, the volume of sediment should encompass the volume of suspension. If the sediment volume is less than the volume of suspension, the supernatant which forms should be clear (indicating a flocculated system).

Chemical Stability—The amount of drug substance must remain within 90–110% of the intended labelled concentration.

% Degradant(s) formed over time—The formation of no more than 5% degradant(s) over a period of 2 years is considered acceptable.

Viscosity—The viscosity should be sufficiently high to hinder rapid sedimentation. However, too high a viscosity is not acceptable from a user's standpoint. An acceptable range is about 200–2500 centipoise, with a preferred range of 400–1000 centipolse.

Density—Ideally, the density of the vehicle will equal the density of the dispersed solids (drug substance); matching vehicle and drug densities will hinder sedimentation. An acceptable range for the formulations of the present invention is 1.10–1.25 g/mL.

Homogeneity—After minimal hand shaking of the package containing suspension, the amount of drug substance present at the top, middle, and bottom of the packaged suspension, will be equivalent within 10%.

Particle Size—Over time the mean particle size of the suspension will remain within 20% of the mean particle size of freshly prepared suspension.

Antimicrobial Efficacy—The suspension will be tested for antimicrobial efficacy via the methods provided in the USP and BP. To be acceptable, the suspension must pass these tests according to the respective specifications.

The formulations of the invention are satisfactory when subjected to the foregoing tests. As will be apparent from the present specification to those skilled in the art, the selection of particular ingredients and their relative concentrations will modify the characteristics balances of the resulting formulations. For example, a 200 mg/mL of mycophenolate mofetil can be suspended in Ora-Plus™ combined with Ora-Sweet™, but, the characteristics balance of the resulting formulation is unacceptably viscous and expected to have too much drug dissolved in the continuous aqueous phase giving rise to increased degradant formation and loss of chemical stability (given the pH of the vehicles, i.e., below 5.0, the lowest acceptable pH for mycophenolate mofetil in the present formulations).

Administration

The formulations of the present invention are useful for oral administration in any oral treatment regimen for mycophenolate mofetil or mycophenolic acid. While human dosage levels have yet to be finalized, generally, a daily dose of mycophenolate mofetil or mycophenolic acid is from about 2.0 to 5.0 grams, preferably about 2.0 to 3.5 grams, which is equivalent to about 25 to 75 mg/kg/day, preferably about 25 to 50 mg/kg/day. The amount of active compound administered will, of course, be dependent on the subject and disease state being treated, the severity of the affliction, the manner and schedule of administration and the judgment of the prescribing physician. For example, a treatment regimen for administering 3.0 grams of mycophenolate mofetil per day, which previously entailed taking 12 capsules (250 mg) (e.g., six, twice daily), when administered with a formulation of the present invention entails taking one 7.5 mL dose (e.g., a spoonfull) twice daily. The formulations of the present invention are also particularly well suited to administration via gastric lavage.

Utility

The formulations of the present invention are useful for the administration of mycophenolate mofetil or mycophenolic acid (the "compounds") as immunosuppressive agents, anti-inflammatory agents, anti-tumor agents, anti-proliferative agents, anti-viral agents and anti-psoriatic agents (as discussed in greater detail below) in mammals, whether domestic (cattle, pigs, sheep, goats, horses), pets (cats, dogs), or preferably humans. The compounds are inhibitors of inosine monophosphate dehydrogenase (IMPDH) and thus inhibit de novo purine synthesis; they have anti-proliferative effects (e.g., against smooth muscle cells and both B and T lymphocytes) and inhibit antibody formation and the glycosylation of cell adhesion molecules in lymphocytes and endothelial cells.

As immunosuppressive agents, the compounds are useful in treating auto-immune related disorders, for example: Type I Diabetes Mellitus; Inflammatory Bowel Disease (e.g., Crohn's Disease and Ulcerative Coliris); Systemic Lupus Erythematosus; Chronic Active Hepatitis; Multiple Sclerosis; Graveis Disease; Hashimoto's Thyroiditis; Behcet's Syndrome; Myasthenia Gravis; Sjogren's Syndrome; Pernicious Anemia; Idiopathic Adrenal Insufficiency; and Polyglandular Autoimmune Syndromes Type I and II.

The compounds are also useful as therapeutic immunosuppressive agents in the treatment of Asthma, Immunohemolytic Anemia, Glomerulonephritis, and Hepatitis. Preventative uses of the compounds as imunosuppressive agents include the treatment of allograft rejection, for example, in cardiac, lung, pancreatic, renal, liver, skin and corneal allografts, and prevention of Graft vs. Host Disease.

The compounds are useful for inhibiting proliferative responses to vascular injury, for example, stenosis following an insult to a blood vessel wall in post-angioplasty restenosis, and post-cardiac by-pass surgery restenosis.

The compounds are useful as anti-inflammatory agents, for example, in treating Rheumatoid Arthritis, Juvenile Rheumatoid Arthritis and Uveitis.

As anti-tumor agents, the compounds are useful in treating solid tumors and malignancies of lymphoreticular origin. For example, the compounds' utility for treatment of solid tumors includes: cancers of the head and neck, including squamous cell carcinoma; lung cancer, including small cell and non-small cell lung carcinoma; mediastinal tumors; esophageal cancer, including squamous cell carcinoma and adenocarcinoma; pancreatic cancer; cancer of the hepatobiliary system, including hepatocellular carcinoma, cholangiocarcinoma, gall bladder carcinoma and biliary tract carcinoma; small intestinal carcinoma, including adenocarcinoma, sarcoma, lymphoma and carcinoids; colorectal cancer, including colon carcinoma and rectal carcinoma; metastatic carcinoma; cancers of the genitourinary system, including ovarian cancer, uterine sarcoma, and renal cell, ureteral, bladder, prostate, urethral, penile, testicular, vulvar, vaginal, cervical, endometrial, and fallopian tube carcinoma; breast cancer; endocrine system cancer; soft tissue sarcomas; malignant mesotheliomas; skin cancer, including squamous cell carcinoma, basal cell carcinoma and melanoma; cancer of the central nervous system; malignant bone tumors; and plasma cell neoplasms.

As anti-tumor agents for the treatment of malignancies of lymphoreticular origin, the compounds are useful in treating, for example: Lymphomas and Leukemias, including B, T and promonocyte cell line malignancies, Mycoses Fungoides, Non-Hodgkins Lymphoma, Malignancies of Burkitt Lymphoma Cells and other EBV-transformed B-lymphocytes, Lymphomas resulting from Epstein-Barr viral infections in allograft recipients, Chronic Lymphocytic Leukemia, Acute Lymphocytic Leukemia and Hairy Cell Leukemia.

As anti-vital agents, the compounds are useful in treating, for example: retroviruses, including Muman T-leukemia Viruses, Types I and II (HTLV-1 and HTLV-2), Human Immuno Deficiency Viruses, Types I and II (HIV-1, HIV-2) and, Human Nasopharyngeal Carcinoma Virus (NPCV) and in treating Herpes Viruses, including EBV infected B-lymphocytes, CMV infection, Herpes Virus Type 6, Herpes Simplex, Types 1 and 2, (HSV-1, HSV-2) and Herpes Zoster.

As anti-psoriatic agents, the compounds are useful in treating, for example, psoriasis and psoriatic arthritis.

EXAMPLES

The following preparations and examples are given to enable those skilled in the art to more clearly understand and to practice the present invention. They should not be considered as limiting the scope of the invention, but merely as being illustrative and representative thereof.

Examples 1–100

These examples illustrate the preparation of high dose oral suspension formulations.

In Examples 1–11, the formulation was manufactured by one of the following alternative methods:

Method A.
1. To heated water, hydroxypropylmethylcellulose was added and dispersed.
2. Microcrystalline cellulose was added to the dispersion of #1 and dispersed.
3. Xanthan gum was added to the mixture of #2 and dispersed.
4. The sweeteners, flavors, color dyes and lecithin were added individually to the mixture of #3 with mixing.
5. In a small separate aliquot of water, citric acid and sodium phosphate dibasic were dissolved, then added to the mixture of step 4, adjusting pH as indicated.
6. In a small separate aliquot of water (heated to 80° C.), methyl paraben and propylparaben were dissolved, then added to the mixture of step 5.
7. Mycophenolate mofetil was added to the mixture of step 6 and mixed well to form a suspension suitable for oral administration.

Method B.
1. To heated water (70°–75° C.), methyl paraben was dissolved with mixing.
2. Microcrystalline cellulose was added to the dispersion of #1 and dispersed.
3. The sorbitol solution was added and mixed to the dispersion of #2. Xanthan gum was added to the mixture and dispersed. This was followed by addition of the maltitol solution with mixing.
4. In a separate vessel containing purified water, citric acid was added and dissolved, followed by the addition and dissolution of sodium phosphate dibasic, anhydrous. This was followed by the dissolution of sucrose and the addition and dispersion of soy lecithin. Mycophenolate mofetil was added and dispersed.
5. The dispersions of steps 3 and 4 were combined and mixed.
6. A stock solution of the dye was prepared. The dye and flavor were added to the dispersion of step 5, with mixing.
7. The dispersion of step 6 was brought to volume with purified water, as necessary.

Example 1

| Ingredient | wt/vol % |
| --- | --- |
| Mycophenolate mofetil | 20 |
| Hydroxypropylmethylcellulose | 0.25 |
| Microcrystalline cellulose | 0.25 |
| Xanthan gum | 0.1 |
| Sorbitol, 70% solution | 50 |
| Sucrose | 10 |
| Lycasin* (maltitol syrup) | 10 |
| Lecithin | 0.1 |
| Methyl paraben | 0.036 |
| Propyl paraben | 0.004 |
| Grape flavor | 1.0 |
| Anise flavor | 0.01 |
| Color (red 28:blue 1, 90:10) | 0.005 |
| Buffer | |
| Citric acid | 0.241 |
| Sodium phosphate dibasic | 0.547 |
| | pH 6 |
| Purified water | q.s. to 100 |

Example 2

| Ingredient | wt/vol % |
| --- | --- |
| Mycophenolate mofetil | 20 |
| Hydroxypropylmethylcellulose | 0.25 |
| Microcrystalline cellulose | 0.25 |
| Xanthan gum | 0.1 |
| Sorbitol, 70% solution | 50 |

-continued

| Ingredient | wt/vol % |
|---|---|
| Sucrose | 10 |
| Lycasin* (maltitol syrup) | 10 |
| Lecithin | 0.1 |
| Methyl paraben | 0.036 |
| Propyl paraben | 0.004 |
| Grape flavor | 1.0 |
| Anise flavor | 0.01 |
| Color (red 28:blue 1, 90:10) | 0.005 |
| Buffer | |
| Citric acid | 0.0542 |
| Sodium phosphate dibasic | 0.673 |
| | pH 7 |
| Purified water | q.s. to 100 |

Example 3

| Ingredient | wt/vol % |
|---|---|
| Mycophenolate mofetil | 20 |
| Hydroxypropylmethylcellulose | 0.25 |
| Microcrystalline cellulose | 0.25 |
| Xanthan gum | 0.1 |
| aspartame | 0.2 |
| Lycasin* (maltitol syrup) | 50 |
| methyl paraben | 0.1 |
| Grape flavor | 1.0 |
| Anise flavor | 0.01 |
| Color (red 28:blue 1, 90:10) | 0.005 |
| Buffer | |
| Citric acid | 0.0542 |
| Sodium phosphate dibasic | 0.673 |
| | pH 7 |
| Purified water | q.s. to 100 |

Example 4

| Ingredient | wt/vol % |
|---|---|
| Mycophenolate mofetil | 20 |
| Hydroxypropylmethylcellulose | 0.2 |
| Microcrystalline cellulose | 0.2 |
| Xanthan gum | 0.075 |
| Sorbitol, 70% solution | 50 |
| Sucrose | 10 |
| Lycasin* (maltitol syrup) | 10 |
| Lecithin | 0.1 |
| Grape flavor | 1.0 |
| Anise flavor | 0.01 |
| Color (red 28:blue 1, 90:10) | 0.005 |
| Buffer | |
| Citric acid | 0.0962 |
| Sodium phosphate dibasic | 0.219 |
| | pH 6 |
| Purified water | q.s. to 100 |

Example 5

| Ingredient | wt/vol % |
|---|---|
| Mycophenolate mofetil | 20 |
| Hydroxypropylmethylcellulose | 0.25 |
| Microcrystalline cellulose | 0.25 |
| Xanthan gum | 0.1 |
| Sorbitol, 70% solution | 50 |

-continued

| Ingredient | wt/vol % |
|---|---|
| Sucrose | 10 |
| Lycasin* (maltitol syrup) | 10 |
| Lecithin | 0.1 |
| Grape flavor | 1.0 |
| Anise flavor | 0.01 |
| Color (red 28:blue 1, 90:10) | 0.005 |
| Buffer | |
| Citric acid | 0.0217 |
| Sodium phosphate dibasic | 0.269 |
| | pH 7 |
| Purified water | q.s. to 100 |

Example 6

| Ingredient | wt/vol % |
|---|---|
| Mycophenolate mofetil | 20 |
| Hydroxypropylmethylcellulose | 0.35 |
| Microcrystalline cellulose | 0.3 |
| Xanthan gum | 0.125 |
| Sorbitol, 70% solution | 30 |
| Sucrose | 10 |
| Lycasin* (maltitol syrup) | 30 |
| Grape flavor | 0.75 |
| Anise flavor | 0.01 |
| Color (red 28:blue 1, 90:10) | 0.005 |
| Buffer | |
| Citric acid | 0.0217 |
| Sodium phosphate dibasic | 0.269 |
| | pH 7 |
| Purified water | q.s to 100 |

Example 7

| Ingredient | wt/vol % |
|---|---|
| Mycophenolate mofetil | 20 |
| Hydroxypropylmethylcellulose | 0.25 |
| Microcrystalline cellulose | 0.25 |
| Xanthan gum | 0.1 |
| Sorbitol, 70% solution | 30 |
| Sucrose | 10 |
| Lycasin* (maltitol syrup) | 30 |
| Lecithin | 0.1 |
| Grape flavor | 1.0 |
| Anise flavor | 0.01 |
| Magnasweet* | 0.2 |
| Color (red 28:blue 1, 90:10) | 0.005 |
| Buffer | |
| Citric acid | 0.142 |
| Sodium phosphate dibasic | 0.438 |
| | pH 6 |
| Purified water | q.s. to 100 |

Example 8

| Ingredient | wt/vol % |
|---|---|
| Mycophenolate mofetil | 20 |
| Microcrystalline cellulose | 0.2 |
| Xanthan gum | 0.1 |
| Sorbitol, 70% solution | 30 |
| Lycasin* (maltitol syrup) | 30 |
| Lecithin | 0.1 |

-continued

| Ingredient | wt/vol % |
|---|---|
| methyl paraben | 0.1 |
| berry flavor | 0.3 |
| Color (red 28:blue 1, 90:10) | 0.005 |
| Buffer | |
| Citric acid | 0.0217 |
| Sodium phosphate dibasic | 0.269 |
| | pH 7 |
| Purified water | q.s. to 100 |

Example 9

| Ingredient | wt/vol % |
|---|---|
| Mycophenolate mofetil | 20 |
| Microcrystalline cellulose | 0.2 |
| Xanthan gum | 0.1 |
| Sorbitol, 70% solution | 50 |
| Sucrose | 10 |
| Lycasin* (maltitol syrup) | 10 |
| Lecithin | 0.1 |
| methyl paraben | 0.1 |
| orange flavor | 0.1 |
| Color (yellow 6) | 0.19 |
| Buffer | |
| Citric acid | 0.06 |
| Sodium phosphate dibasic | 0.7 |
| | pH 7 |
| Purified water | q.s. to 100 |

Example 10

| Ingredient | wt/vol % |
|---|---|
| Mycophenolate mofetil | 20 |
| Microcrystalline cellulose | 0.2 |
| Sucrose | 10 |
| Lycasin* (maltitol syrup) | 60 |
| Lecithin | 0.1 |
| mixed fruit flavor | 0.2 |
| Color (yellow 6:red 3, 15:85) | 0.001 |
| Citric acid | 0.06 |
| Sodium phosphate dibasic | 0.7 |
| Purified water | q.s. to 100 |

Example 11

| Ingredient | wt/vol % |
|---|---|
| Mycophenolate mofetil | 20 |
| microcrystalline cellulose | 0.2 |
| xanthan gum | 0.1 |
| Sorbitol, 70% solution | 50 |
| Sucrose | 10 |
| Lycasin* (maltitol syrup) | 10 |
| soy Lecithin | 0.1 |
| citric acid | 0.06 |
| sodium phosphate dibasic | 0.7 |
| methyl paraben | 0.1 |
| mixed fruit flavor | 0.2 |
| Color (yellow 6:red 3, 15:85) | 0.001 |
| Purified water | q.s. to 100 |

Examples 12–24 illustrate the preparation of a dry granulation or powder blend. In these Examples, the formulation was manufactured by one of the following alternative methods:

Methods A:

1. Mycophenolate mofetil, sweetener(s), wetting agent(s), suspending and/or viscosity increasing agent(s), flavor(s) and antimicrobial agent(s) are weighed and combined in a mixer.
2. The dye(s) and buffer(s) are dissolved in water.
3. The solution of step (2) is added to the mixer bowl of step (1), until a desired granulation size is obtained.
4. The granulation is dried then milled to reduce particle size.
5. Using a blender, the suspending and/or viscosity increasing agent(s) is/are added.

Method B:

In a suitable mixer, combine and mix all ingredients to prepare a direct blend of the formulation.

Example 12

| Ingredient | mg |
|---|---|
| mycophenolate mofetil | 3,000 |
| sodium carboxymethylcellulose | 300 |
| sorbitol, powder | 3,000 |
| maltitol | 7,500 |
| pluronic F68 | 60 |
| mint | 150 |
| FD&C green 3 | 0.1 |

The dry granulation or powder blend is suitable for use as a pharmaceutical formulation by the addition of purified water followed by shaking to form a suspension having 3.0 grams of mycophenolate mofetil in a final volume of 15 ml.

Example 13

| Ingredient | mg |
|---|---|
| mycophenolate mofetil | 3,000 |
| sodium carboxymethylcellulose | 300 |
| mannitol | 6,000 |
| aspartame | 45 |
| pluronic F68 | 60 |
| sodium methyl paraben | 30 |
| cherry | 150 |
| FD&C red 40 | 0.15 |
| FD&C blue 1 | 0.015 | in a container marked to be filled with purified water to a final predetermined volume of 15 ml.

Example 14

| Ingredient | mg |
|---|---|
| mycophenolate mofetil | 3,000 |
| sodium carboxymethylcellulose | 300 |
| sorbitol, powder | 15,000 |
| pluronic F68 | 60 |
| cherry | 150 |
| FD&C red 40 | 0.15 |
| FD&C blue 1 | 0.015 | in a container marked to be filled with purified water to a final predetermined volume of 15 ml.

Example 15

| Ingredient | mg |
| --- | --- |
| mycophenolate mofetil | 3,000 |
| sodium carboxymethylcellulose | 300 |
| mannitol | 6,000 |
| aspartame | 45 |
| potassium sorbate | 75 |
| pluronic F68 | 60 |
| cherry | 150 |
| FD&C red 40 | 0.15 |
| FD&C blue 1 | 0.015 | in a container marked to be filled with purified water to a final predetermined volume of 15 ml.

Example 16

| Ingredient | mg |
| --- | --- |
| mycophenolate mofetil | 3,000 |
| xanthan gum | 15 |
| colloidal silicon dioxide | 75 |
| soy lecithin | 15 |
| sorbitol | 8,250 |
| aspartame | 7.5 |
| sodium methyl paraben | 30 |
| berry flavor | 45 |
| color (FD&C red #3 | 0.45 |
| FD&C blue #1 | 0.09 | in a container marked to be filled with purified water to a final predetermined volume of 15 mL.

Example 17

| Ingredient | mg |
| --- | --- |
| mycophenolate mofetil | 3,000 |
| xanthan gum | 15 |
| colloidal silicon dioxide | 75 |
| soy lecithin | 15 |
| sorbitol | 4,500 |
| aspartame | 15 |
| citric acid | 16.5 |
| sodium citrate | 150 |
| sodium methyl paraben | 30 |
| berry flavor | 45 |
| color (FD&C red #3 | 0.45 |
| FD&C blue #1 | 0.09 | in a container marked to be filled with purified water to a final predetermined volume of 15 mL.

Example 18

| Ingredient | mg |
| --- | --- |
| mycophenolate mofetil | 3,000 |
| xanthan gum | 15 |
| colloidal silicon dioxide | 75 |
| soy lecithin | 15 |
| sorbitol | 8,250 |
| aspartame | 7.5 |
| citric acid | 16.5 |
| sodium citrate | 150 |
| sodium methyl paraben | 34.5 |
| mixed fruit flavor | 30 |
| color (FD&C red #3 | 0.132 |
| FD&C yellow #6) | 0.0285 | in a container marked to be filled with purified water to a final predetermined volume of 15 mL.

Example 19

This example illustrates a dry granulation of the invention, provided as in a container marked to be filled with purified water to a final predetermined volume of 450 mL.

| Ingredient | mg/ml* |
| --- | --- |
| mycophenolate mofetil | 90,000 |
| sodium carboxymethylcellulose | 9,000 |
| sorbitol | 135,000 |
| sucrose | 45,000 |
| pluronic F68 | 1,800 |
| potassium sorbate | 2,250 |
| cherry | 4,500 |
| color (red 40:blue 1, 90:10) | 4.5 |

Example 20

| Ingredient | mg/ml* |
| --- | --- |
| mycophenolate mofetil | 200.0 |
| xanthan gum | 1.0 |
| colloidal silicon dioxide | 5.0 |
| soy lecithin | 1.0 |
| sorbitol | 400.0 |
| aspartame | 1.0 |
| citric acid | 1.1 |
| sodium citrate | 10.0 |
| sodium methyl paraben | 2.0 |
| berry flavor | 3.0 |
| color (FD&C red #3 | 0.034 |
| FD&C blue #1) | 0.006 |

(*concentration after constitution with water)

Example 21

| Ingredient | mg/ml* |
| --- | --- |
| mycophenolate mofetil | 200.0 |
| xanthan gum | 1.5 |
| colloidal silicon dioxide | 10.0 |
| soy lecithin | 2.0 |
| sorbitol | 300.0 |
| aspartame | 2.0 |
| citric acid | 1.1 |
| sodium citrate | 10.0 |
| sodium methyl paraben | 1.0 |
| orange flavor | 1.0 |
| color (FD&C yellow #6) | 0.1 |

(*concentration after constitution with water)

Example 22

| Ingredient | mg/ml* |
| --- | --- |
| mycophenolate mofetil | 200.0 |
| xanthan gum | 1.0 |

-continued

| Ingredient | mg/ml* |
|---|---|
| colloidal silicon dioxide | 5.0 |
| soy lecithin | 1.0 |
| sorbitol | 550.0 |
| citric acid | 1.1 |
| sodium citrate | 10.0 |
| sodium methyl paraben | 2.0 |
| berry flavor | 3.0 |
| color (FD&C red #3 | 0.034 |
| FD&C blue #1) | 0.006 |

(*concentration after constitution with water)

Example 23

| Ingredient | mg/ml* |
|---|---|
| mycophenolate mofetil | 200.0 |
| xanthan gum | 0.5 |
| colloidal silicon dioxide | 10.0 |
| soy lecithin | 2.0 |
| sorbitol | 400.0 |
| aspartame | 1.0 |
| citric acid | 1.1 |
| sodium citrate | 10.0 |
| sodium methyl paraben | 2.3 |
| mixed fruit flavor | 2.0 |
| color (FD&C red #3 | 0.008 |
| FD&C yellow #6) | 0.002 |

(*concentration after constitution with water)

Example 24

| Ingredient | mg/ml* |
|---|---|
| mycophenolate mofetil | 200.0 |
| xanthan gum | 1.5 |
| colloidal silicon dioxide | 10.0 |
| soy lecithin | 2.0 |
| sorbitol | 400.0 |
| aspartame | 1.0 |
| citric acid | 1.1 |
| sodium citrate | 10.0 |
| sodium methyl paraben | 2.3 |
| orange flavor | 1.0 |
| color (FD&C yellow #6) | 0.19 |

(*concentration after constitution with water)

Examples 25–37

By following the procedures of Examples 12–24 and adjusting the amounts accordingly, there are obtained the corresponding respective dry granulations or powder blends which when mixed with purified water in a container marked to be filled to a predetermined volume of 240 mL (8 oz) provide a 240 mL or 8 oz size.

Examples 38–50

By following the procedures of Examples 12–24 and adjusting the amounts accordingly, there are obtained the corresponding respective dry granulations or powder blends which when mixed with purified water in a container marked to be filled to a predetermined volume of 120 mL (4 oz) provide a 120 mL or 4 oz size.

Examples 51–100

By following the procedures of Examples 1–50 and substituting mycophenolate mofetil with mycophenolic acid, there are obtained the corresponding respective suspensions and dry granulations or powder blends.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A pharmaceutical formulation comprising:

| Ingredient | % wt/vol |
|---|---|
| mycophenolate mofetil | 20 |
| hydroxypropylmethylcellulose | 0.25 |
| microcrystalline cellulose | 0.25 |
| xanthan gum | 0.1 |
| sorbitol, 70% solution | 30–50 |
| maltitol syrup | 10–30 |
| sucrose | 0–10 |
| fructose | 0–10 |
| aspartame | 0–0.5 |
| lecithin | 0–0.1 |
| citric acid | 0.02–0.25 |
| sodium phosphate dibasic | 0.19–0.67 |
| methyl paraben | 0–0.20 |
| propyl paraben | 0–0.02 |
| flavor | 0.3–1.0 |
| flavor enhancer/bitter maskant | 0–1 |
| color | 0.005 |
| purified water | q.s. to 100 | as a liquid suspension suitable for oral administration.

2. A pharmaceutical formulation consisting essentially of:

| Ingredient | % wt/vol |
|---|---|
| mycophenolate mofetil | 20 |
| hydroxypropylmethylcellulose | 0.25 |
| microcrystalline cellulose | 0.25 |
| xanthan gum | 0.1 |
| sorbitol solution | 50 |
| sucrose | 10 |
| maltitol syrup | 10 |
| lecithin | 0.1 |
| methyl paraben | 0.036 |
| propylparaben | 0.004 |
| grape | 1.0 |
| anise | 0.01 |
| color (red 28: blue 1, 90:10) | 0.005 |
| citric acid | 0.0542 |
| sodium phosphate dibasic | 0.673 |
| purified water | q.s. to 100 | adjusted to a pH of 7, as a liquid suspension suitable for oral administration.

3. A pharmaceutical formulation comprising:

| Ingredient | % wt/vol |
|---|---|
| mycophenolate mofetil | 20 |
| microcrystalline cellulose | 0.2 |
| xanthan gum | 0.1 |
| sorbitol, 70% solution | 30–50 |
| maltitol syrup | 10–30 |

-continued

| Ingredient | % wt/vol |
|---|---|
| sucrose | 0–10 |
| fructose | 0–10 |
| aspartame | 0–0.5 |
| lecithin | 0–0.5 |
| citric acid | 0.02–0.25 |
| sodium phosphate dibasic | 0.15–1.0 |
| methyl paraben | 0–0.2 |
| propyl paraben | 0–0.02 |
| flavor | 0.1–3.0 |
| flavor enhancer/bitter maskant | 0–1 |
| color | 0.02 |
| purified water | q.s. to 100 | as a liquid suspension suitable for oral administration.

4. The pharmaceutical formulation of claim 3, consisting essentially of:

| Ingredient | % wt/vol |
|---|---|
| mycophenolate mofetil | 20 |
| microcrystalline cellulose | 0.2 |
| xanthan gum | 0.1 |
| sorbitol, 70% solution | 50 |
| maltitol syrup | 10 |
| sucrose | 10 |
| soy lecithin | 0.1 |
| citric acid | 0.06 |
| sodium phosphate dibasic | 0.7 |
| methyl paraben | 0.04 |
| flavor | ≦0.3 |
| color | <0.02 |
| purified water | q.s. to 100 | adjusted to a pH of 7, as a liquid suspension suitable for oral administration.

5. A process for the preparation of a pharmaceutical formulation comprising:

| Ingredient | % wt/vol |
|---|---|
| mycophenolate mofetil or mycophenolic acid | 7.5–30.0 |
| suspending/viscosity agent | 0.1–3.0 |
| wetting agent | 0–0.5 |
| sweeteners | 30.0–70.0 |
| flavor | 0.1–2.0 |
| flavor enhancer/bitter maskant | 0–1.0 |
| buffering to pH 5.0–7.5 | 0.15–2.0 |
| antimicrobial agent | 0–10.0 |
| color | 0–0.03 |
| purified water | q.s. to 100 | as a liquid suspension for oral administration, the process comprising:

I. a. adding and dispersing the antimicrobial agent to heated water, followed by adding the suspending and/or viscosity agent(s);
   b. dissolving, with mixing, the buffer(s), followed by adding the sweetener(s), wetting agent(s), dye(s), flavor enhancer(s), and flavor(s); and
   c. adding the active compound to the mixture from step b, followed by mixing the liquids well to form a suspension; or II. a. adding and dissolving with mixing the antimicrobial agent and water;
   b. dispersing the suspending and/or viscosity increasing agent(s) in the dispersion of step a;
   c. adding with mixing the sweetener(s) to the dispersion of step b; followed by adding the suspending and/or viscosity agent(s) with mixing; followed by adding the sweetener(s) with mixing;
   d. dissolving the buffer(s) in water, followed by adding and dissolving sweetener(s), followed by adding and dispersing the wetting agent(s), followed by adding and dispersing the active compound;
   e. combining the dispersions of steps c and d with mixing;
   f. adding the dye(s) and flavor(s) to the dispersion of step e; and
   g. bringing the dispersion of step f to volume with purified water.

6. A pharmaceutical formulation comprising:

| Ingredient | mg/mL |
|---|---|
| mycophenolate mofetil | 200 |
| xanthan gum | 0.5–1.5 |
| colloidal silicon dioxide | 5–10 |
| soy lecithin | 1–2 |
| sorbitol | 0–550 |
| aspartame | 0–3 |
| citric acid | 0–1.5 |
| sodium citrate | 0–20 |
| sodium methyl paraben | 0–10 |
| flavor | 0.1–3 |
| color (to complement the flavor) | 0–0.2 | as a dry granulation or powder blend suitable, when constituted with water, for forming a suspension for oral administration, where mg/mL represents concentration after constitution with water.

7. The pharmaceutical formulation of claim 6 provided in a container marked to be filled with purified water to a final predetermined volume.

8. The pharmaceutical formulation of claim 7, comprising:

| Ingredient | mg |
|---|---|
| mycophenolate mofetil | 90,000 |
| xanthan gum | 450 |
| colloidal silicon dioxide | 2,250 |
| soy lecithin | 450 |
| sorbitol | 247,500 |
| aspartame | 225 |
| sodium methyl paraben | 900 |
| berry flavor | 1,350 |
| color | |
| (FD&C red #3 | 13.5 |
| FD&C blue #1 | 2.7 | in a container marked to be filled with purified water to a final predetermined volume of 450 mL.

9. The pharmaceutical formulation of claim 7, comprising:

| Ingredient | mg |
|---|---|
| mycophenolate mofetil | 90,000 |
| xanthan gum | 450 |
| colloidal silicon dioxide | 2,250 |
| soy lecithin | 450 |
| sorbitol | 135,000 |
| aspartame | 450 |
| citric acid | 495 |
| sodium citrate | 4,500 |
| sodium methyl paraben | 900 |
| berry flavor | 1,350 |

-continued

| Ingredient | mg |
|---|---|
| color | |
| (FD&C red #3 | 13.5 |
| FD&C blue #1) | 2.7 | in a container marked to be filled with purified water to a final predetermined volume of 450 mL.

10. The pharmaceutical formulation of claim 7, comprising:

| Ingredient | mg |
|---|---|
| mycophenolate mofetil | 90,000 |
| xanthan gum | 675 |
| colloidal silicon dioxide | 4,500 |
| soy lecithin | 900 |
| sorbitol | 180,000 |
| aspartame | 450 |
| sodium methyl paraben | 1,035 |
| mixed fruit flavor | 900 |
| color | |
| (FD&C red #3 | 3.6 |
| FD&C yellow #6) | 0.9 | in a container marked to be filled with purified water to a final predetermined volume of 450 mL.

11. The pharmaceutical formulation of claim 7, comprising:

| Ingredient | mg |
|---|---|
| mycophenolate mofetil | 90,000 |
| xanthan gum | 450 |
| colloidal silicon dioxide | 2,250 |
| soy lecithin | 450 |
| sorbitol | 247,500 |
| aspartame | 225 |
| citric acid | 495 |
| sodium citrate | 4,500 |
| sodium methyl paraben | 1,035 |
| mixed fruit flavor | 900 |
| color | |
| (FC&C red #3 | 3.96 |
| FD&C yellow #6) | 0.855 | in a container marked to be filled with purified water to a final predetermined volume of 450 mL.

12. The pharmaceutical formulation of claim 7, comprising

| Ingredient | mg |
|---|---|
| mycophenolate mofetil | 45,000 |
| xanthan gum | 225 |
| colloidal silicon dioxide | 1,125 |
| soy lecithin | 225 |
| sorbitol | 123,750 |
| aspartame | 112.5 |
| citric acid | 247.5 |
| sodium citrate | 2,250 |
| sodium methyl paraben | 517.5 |
| mixed fruit flavor | 450 |

-continued

| Ingredient | mg |
|---|---|
| color | |
| (FD&C red #3 | 1.98 |
| FD&C yellow #6) | 0.43 | in a container marked to be filled with purified water to a final predetermined volume of 240 mL.

13. The pharmaceutical formulation of claim 7, comprising

| Ingredient | mg |
|---|---|
| mycophenolate mofetil | 22,500 |
| xanthan gum | 112.5 |
| colloidal silicon dioxide | 562.5 |
| soy lecithin | 112.5 |
| sorbitol | 61,875 |
| aspartame | 56.25 |
| citric acid | 123.75 |
| sodium citrate | 1,125 |
| sodium methyl paraben | 258.75 |
| mixed fruit flavor | 225 |
| color | |
| (FD&C red #3 | 0.99 |
| FD&C yellow #6) | 0.22 | in a container marked to be filled with purified water to a final predetermined volume of 120 mL.

14. The pharmaceutical formulation of claim 7, comprising:

| Ingredient | mg |
|---|---|
| mycophenolate mofetil | 90,000 |
| xanthan gum | 675 |
| colloidal silicon dioxide | 4,500 |
| soy lecithin | 900 |
| sorbitol | 180,000 |
| aspartame | 450 |
| citric acid | 495 |
| sodium citrate | 4,500 |
| sodium methyl paraben | 1,035 |
| orange flavor | 450 |
| color (FD&C yellow #6) | 90 | in a container marked to be filled with purified water to a final predetermined volume of 450 mL.

15. A pharmaceutical formulation, comprising:

| Ingredient | mg/mL |
|---|---|
| mycophenolate mofetil | 200 |
| sodium carboxymethylcellulose | 20 |
| sorbitol | 300 |
| sucrose | 100 |
| pluronic F68 | 4 |
| potassium sorbate | 5.0 |
| cherry | 10 |
| color (red 40:blue 1, 90:10) | 0.01 | as a dry granulation or powder blend suitable, when constituted with water, for forming a suspension for oral administration, where mg/mL represents concentration after constitution with water.

16. The pharmaceutical formulation of claim 15 provided in a container marked to be filled with purified water to a final predetermined volume.

17. The pharmaceutical formulation of claim 16, comprising:

| Ingredient | mg |
|---|---|
| mycophenolate mofetil | 90,000 |
| sodium carboxymethylcellulose | 9,000 |
| sorbitol | 135,000 |
| sucrose | 45,000 |
| pluronic F68 | 1,800 |
| postassium sorbate | 2,250 |
| cherry | 4,500 |
| color (red 28:blue 1, 90:10) | 4.5 | in a container marked to be filled with purified water to a final predetermined volume of 450 mL.

18. A process for the preparation of a pharmaceutical formulation comprising:

| Ingredient | mg/mL |
|---|---|
| mycophenolate mofetil or mycophenolic acid | 75–300 |
| suspending/viscosity agent | 1–30 |
| wetting agent | 0–10 |
| sweeteners | 1–1200 |
| flavor | 0.1–100 |
| flavor enhancer/bitter maskant | 0–50 |
| buffering agents | 0–25 |
| antimicrobial agent | 0–10 |
| color | 0–2 | as a dry granulation or powder blend suitable, when constituted with water, for forming a suspension for oral administration, where mg/mL represents concentration after constitution with water, the process comprising:

I. a. combining the active compound, sweetener(s), wetting agent(s), suspending and/or viscosity increasing agent(s), flavor(s) and antimicrobial agent(s) in a mixer;
  b. dissolving the dye(s) and buffer(s) in water;
  c. combining the solution of step (b) to the mixer bowl of step (a) and mixing until a desired granulation size is obtained;
  d. drying the granulation then milling to reduce particle size;
  e. adding the suspending and/or viscosity increasing agent(s) to the granulation of step (d) using a blender; or II. a. combining the active compound, sweetener(s), wetting agent(s), suspending and/or viscosity increasing agent(s), dye(s), and buffer(s) and mixing to form a powder blend.

\* \* \* \* \*